United States Patent [19]

Counsell et al.

[11] 4,241,088

[45] Dec. 23, 1980

[54] 1-(TRIALKYLAMINO)-3-(PHENYLPHENOX-Y)-2-PROPANOL QUARTERNARY SALTS

[75] Inventors: Raymond E. Counsell; Benedict R. Lucchesi, both of Ann Arbor, Mich.

[73] Assignee: The Regents of the University of Michigan, Ann Arbor, Mich.

[21] Appl. No.: 780,880

[22] Filed: Mar. 24, 1977

Related U.S. Application Data

[63] Continuation of Ser. No. 623,767, Oct. 20, 1975, abandoned.

[51] Int. Cl.$^3$ .............................................. A61K 31/165
[52] U.S. Cl. ...................................... 424/329; 564/287
[58] Field of Search ................. 424/329; 260/567.6 M

[56] References Cited

U.S. PATENT DOCUMENTS

| | | | |
|---|---|---|---|
| 3,328,464 | 6/1967 | Gündel | 260/567.6 |
| 3,840,666 | 10/1974 | Lucchesi | 424/329 |

FOREIGN PATENT DOCUMENTS 1197755  7/1970  United Kingdom .......... 260/570.7 OH

*Primary Examiner*—Frederick E. Waddell
*Attorney, Agent, or Firm*—Olsen and Stephenson

[57] ABSTRACT

The above captioned compounds exhibit potent and long acting anti-arrhythmic activity while lacking the undesirable side effects, e.g. β-adrenergic receptor blocking activity and local anesthetic activity, characteristic of related prior art compounds.

2 Claims, No Drawings

1-(TRIALKYLAMINO)-3-(PHENYLPHENOXY)-2-PROPANOL QUARTERNARY SALTS

This is a continuation, of application Ser. No. 623,767, filed Oct. 20, 1975, now abandoned.

The present invention is concerned with novel chemical compounds of the following formula

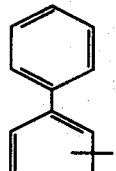
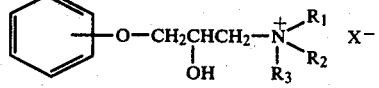

wherein $R_1$, $R_2$, and $R_3$ are lower alkyl and $X^-$ is the anion of a pharmaceutically acceptable non-toxic acid, also novel compositions containing those compounds and the methods for their utilization as anti-arrhythmic agents.

Preferred among those compounds are those in which $R_1$ and $R_2$ are methyl and $R_3$ is isopropyl. Especially preferred are those compounds in which $R_1$ and $R_2$ are methyl, $R_3$ is isopropyl, $X^-$ is halide, and the phenylphenoxy substituent is 2-phenylphenoxy.

Anions of suitable pharmaceutically acceptable non-toxic acids are typified by the halides, e.g. chloride, bromide, iodide, fluoride, the ortho, meta and pyrophosphates, the sulphate and the alkylsulphate which is methylsulphate and ethyl sulphate.

Particularly preferred anions for the purposes of this invention are the iodide and the chloride.

The lower alkyl groups comprehended are the straight chain or branched groups having 1-4 carbon atoms inclusive as illustrated by methyl, ethyl, propyl, isopropyl, and the like.

The instant compounds are manufactured conveniently by a variety of methods. Typically, (2, 3 or 4)-phenylphenol is allowed to react with epichlorohydrin and aqueous sodium or potassium hydroxide to produce intermediates of the formula

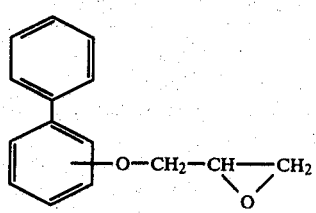

These intermediates are allowed to react with a primary alkyl amine at reflux to afford the corresponding secondary amines of the formula

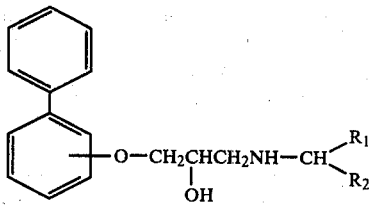

and subsequent treatment with 2 molecular equivalents of the appropriate alkyl halide, sulphate or phosphate affords the desired quarternary compounds of the formula

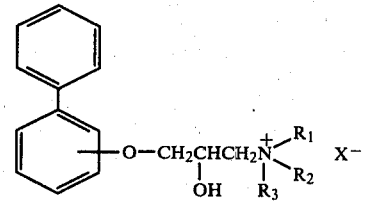

wherein $R_1$, $R_2$, $R_3$ and $X^-$ are defined as hereinbefore.

Alternatively, the intermediates of the formula

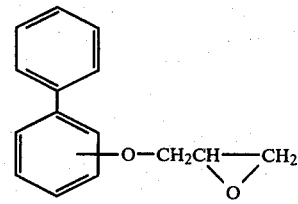

are allowed to react at reflux with an appropriate secondary amine to afford the corresponding tertiary amines of the formula

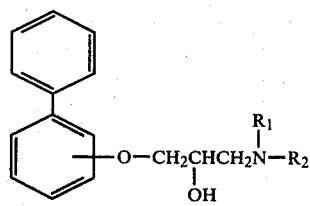

Those compounds then are allowed to react further with a molecular equivalent of the appropriate alkyl halide, sulphate or phosphate, to produce the instant compounds. For example, 1,2-epoxy-3-(2-phenylphenoxy)propane is allowed to react at reflux with methylisopropyl amine to afford the corresponding 1-(N-isopropyl-N-methylamino)-3-(2-phenylphenoxy)-propan-2-ol. This compound then is allowed to react further with a molecular equivalent of methyl chloride to afford [3-(2-phenylphenoxy)-2-hydroxypropyl]isopropyldimethylammonium chloride.

It is apparent that analogous methods of preparation, wherein for example, the methyl groups are added initially, followed by addition of the isopropyl moiety, are available by proper choice of the particular amine at each appropriate stage of the synthesis.

The compounds of the present invention are useful in consequence of their ability to reverse cardiac arrhythmias. They possess, moreover, the advantage of long-acting activity, and they are effective against cardiac rhythm disturbances associated with myocardial ischemia and infarction. These agents are, furthermore, advantageously useful as compared to known anti-arrhythmic agents in that they unexpectedly lack the undesirable β-adrenergic receptor blocking activity of related prior art compounds. A further advantage of the compounds of this invention is their lack of local anesthetic activity and relative lack of persistent cardiovascular depressant effects. The above-described properties are demonstrated in the following assays:

LOCAL ANESTHETIC ACTIVITY: Female frogs (Rana pipiens) are decapitated and the sciatic-tibial-peroneal nerves (sciatic trunk) are removed bilaterally and placed in frog Ringer's solution. The Ringer's solution is of the following composition, expressed as millimoles per liter: NaCl, 111; KCl, 2.7; $CaCl_2.2H_2O$, 1.4; and $NaHCO_3$, 2.4. The solution has a pH of 7.4 and is maintained at a temperature of 25° C. In one series of experiments the epineurium of the nerve is removed by the method of Feng and Liu, *J. Cell. Comp. Physiol.* 34, 1 (1949).

The experimental design has been described in greater detail previously by Lucchesi and Iwami, *J. Pharmacol. Exp. Therap.*, 162, 49 (1968). Briefly, a sciatic trunk is passed through a plastic T-tube, and both are mounted on platinum electrodes in a nerve chamber with a humidified atmosphere. Ringer's solution can then be pumped at a constant rate into the vertical limb of the T-tube. The pump also serves to remove fluid from the chamber at this same rate.

Monophasic spikes are recorded by crushing that part of the nerve in contact with the distal recording electrode. The nerves are stimulated at their peripheral ends so as to produce a maximal spike potential for the A α group of fibers. Since the height of the spike is an index of the number of fibers conducting impulses, and since the response is maximal, any reduction in spike height can be attributed to a block of some fibers in the treated segment. The action potential is amplified through a preamplifier, displayed on an oscilliscope and photographed. Spike potentials are photographed every 15 min. for 1 hour, starting with the time drugs are applied to the nerve trunks. The percent change from control spike amplitude is calculated from the photographed tracings.

TESTS FOR BETA-ADRENERGIC RECEPTOR BLOCKADE: Dogs, 9.2–12.8 kg, are anesthetized with intravenous pentobarbital sodium, 30 mg/kg. The right ventricle is exposed through the 5th right intercostal space; the pericardium is opened and a calibrated Walton-Brodie strain-gauge arch is sutured to the right ventricle. The muscle segment between the feet of the strain-gauge arch is stretched to a length which gives a contraction of maximal amplitude. The animals are respired with room air by means of a Harvard Respirator. Femoral arterial pressure is measured with a Statham P23dB pressure transducer. Heart rate is recorded with a Grass tachometer which is triggered by the electrical signal from the strain-gauge arch. Recordings are made on a Grass model 7 polygraph. All drugs are administered via a cannulated jugular vein.

Changes in heart rate and right ventricular isometric force to geometrically increasing doses of isoproterenol administered intravenously are determined before and after administration of test compound. Each dog thus serves as its own control. Statistical analysis of the data is performed by the method of paired comparisons as described by Hill (1961).

STUDIES OF CARDIOVASCULAR EFFECTS OF TEST COMPOUND HEMO-DYNAMIC MEASUREMENTS: Dogs (13.6 to 17.0 kg), are anesthetized with intravenous pentobarbital sodium, 30 mg/kg. Positive pressure respiration is maintained with a Harvard respirator. The cervical vagi are severed and the jugular vein is cannulated for administration of drugs. The thorax is entered through the fourth right intercostal space; the pericardium is opened and sutured to the chest wall to form a cradle to support the heart. A calibrated Walton-Brodie strain gauge arch is sutured to the right ventricle. Heart rate is recorded by means of a cardiotachometer which is triggered by the electrical signal from the strain gauge arch. Blood pressure is measured from a cannulated femoral artery by means of a Statham P23dB pressure transducer. Cardiac output is determined by the method of thermal dilution using a flow-directed balloon catheter containing a thermistor near its distal tip (Swan-Ganz thermal dilution catheter). The distal tip of the balloon catheter is advanced until it is in a wedge position in the pulmonary artery. The electrical signal from the thermistor is delivered to a Columbus Instrument Cardiac Output Computer. The proximal port of the flow-directed catheter is located in the right atrium. Cardiac outputs are obtained by rapidly injecting 2.0 ml of room temperature 0.9 percent sodium chloride solution into the right atrium. Each determination of cardiac output is the mean of three separate measurements. After obtaining satisfactory baseline recordings, test compound is infused via the jugular vein at a rate of 5 mg/min. Measurements of the various hemo-dynamic parameters are taken when cumulative doses of 1.0; 5.0 and 10.0 mg/kg has been administered to each of the animals.

All data are expressed as the mean±S.E. and are analyzed by the method of paired analysis.

ISOLATED PAPILLARY MUSCLES: Right ventricular papillary muscles are removed rapidly from cats (3.7 to 5.2 kg) anesthetized with pentobarbital sodium, 30 mg/kg intraperitoneally and are suspended in a 50 ml organ bath. The lower nontendinous end of the muscle are held by a spring-loaded Lucite clip fixed to a rigid stainless steel rod. The upper tendinous end of the muscle is tied with a short length of 4-0 braided surgical silk which is connected to a calibrated Grass FT-03 force displacement transducer. The muscles are stimulated electrically through punctate electrodes at a frequency of 30/minute, with square wave stimuli of 1.0 msec duration and a voltage 10 percent greater than threshold. The muscle baths are filled with a solution of the following compositions, expressed as mM/liter: $Na^+$, 143; $Ca^{++}$, 2.5; $K^+$, 5.9; $Mg^{++}$, 1.19; $Cl^-$, 126; $HCO_3^-$, 25.4; $HPO_4^-$, 1.19; and Dextrose 5 mM and adjusted to a pH of 7.4. The solution is maintained at a temperature of 32.5° C. and is bubbled with 95 percent $O_2$ and 5 percent $CO_2$.

Each muscle is stretched to the peak of its length-active tension curve and allowed to stabilize for a period of 2 hours before being exposed to increasing concentrations of test compound. The data are expressed as a percent of initial control force per $mm^2$ of cross sectional area and analyzed by paired analysis. The electrical signal from the force-displacement transducer is differentiated electronically to obtain the rate of force development, dF/dt, expressed as gm/sec/mm$^2$.

OUABAIN-INDUCED ARRHYTHMIAS IN THE ANESTHETIZED DOG: Male, mongrel dogs (8.0 to 13.5 kg) are anesthetized with intravenous pentobarbital sodium, 30 mg/kg. Blood pressure is measured from the femoral artery with a Statham pressure transducer. All drugs are administered into the cannulated left external jugular vein. The right vagus nerve is sectioned and its distal end is stimulated with 1.0 msec square-wave stimuli at a frequency of 40 Hz at 6.0 to 8.0 V.

Ventricular tachycardia is induced by the admintration of ouabain, 40 µg/kg, i.v., followed in 30 minutes by 20 µg/kg and every 15 minutes thereafter by an additional 10 µg/kg until ventricular tachycardia develops.

The criteria used to determine antiarrhythmic activity are: (1) reversion to normal sinus rhythm for a period of not less than 30 minutes; (2) failure of stimulation of the distal right vagus nerve to expose automatic ectopic ventricular activity during the period of vagal-induced sinoatrial arrest; and (3) return of the abnormal rhythm after the intravenous administration of insulin, 80 U, to insure the continued presence of ouabain in concentrations sufficient to induce cardiotoxicity. Lead II electrocardiograms are monitored continuously on an oscilloscope and all recordings are made on a Grass model 7 polygraph.

VENTRICULAR ARRHYTHMIAS AFTER CORONARY ARTERY LIGATION:

ONE-STEP LIGATION: Dogs (8.6 to 16.4 kg) are anesthetized with pentobarbital sodium, 30 mg/kg, i.v. and respired by means of a Harvard respirator. The heart is exposed through the 5th left intercostal space. The pericardium is opened and tied to the chest wall to form a cradle which supports the heart. The left anterior descending coronary artery is dissected free at a point near its origin. A silk suture is passed under the vessel and the free ends are passed through a short section of polyethylene tubing. The artery can be occluded by pressing the tubing onto the vessel while at the same time pulling up on the free ends of the suture. The occlusion can be terminated and blood reinstituted by releasing the suture and pulling the tubing away from the vessel. In these experiments, acute occlusion of the anterior descending coronary artery is maintained for a period of 20 minutes after which the occlusion is released.

Two groups of animals are studies: controls, which receive a saline infusion; and animals treated with test compound in a dose of 10 mg/kg, i.v. The Lead II electrocardiogram and femoral arterial pressure are recorded on magnetic tape (Harvard Physiological Tape Recorder) for subsequent analysis and recording on a Grass model 7 polygraph.

TWO-STEP LIGATION: Mongrel dogs (10.8 to 12.8 kg) are anesthetized with intravenous pentobarbital sodium, 30 mg/kg and placed on positive pressure ventilation with room air via a cuffed endotracheal tube. Under aseptic conditions, a thoracotomy is performed in the 5th, left intercostal space and a 5 to 8 mm segment on the left anterior descending coronary artery is dissected free at a point just below the border of the left atrial appendage. A double ligature is passed under the artery and the vessel is occluded in two stages according to the method described by Harris, Circulation, 1, 1318 (1950). Sterile catheters (0.040 in I.D.) are placed in the external jugular vein and the left carotid artery. These are exteriorized via a small stab wound at the back of the neck and are maintained patent by periodic flushing with sterile heparin solution. The animals are studied 24 and 48 hours later in the unanesthetized state. The Lead II electrocardiogram and arterial blood pressure are continuously recorded while the animals are supported in a harness and maintained in a quiet environment. Test compound is administered at a constant infusion rate of 5 mg/min via the jugular vein catheter. The electrocardiographic recordings are analyzed according to the method of Moran et al. (1962), in which only beats of sinoatrial origin are considered as normal and all other QRS complexes are classified as ectopic.

DETERMINATION OF VENTRICULAR FIBRILLATION THRESHOLD: These experiments are performed on mongrel dogs (10.2 to 11.6 kg) anesthetized with pentobarbital sodium, 30 mg/kg, i.v. The animals are maintained by positive pressure respiration by a Harvard respirator pump. The heart is exposed through a thoracotomy in the 5th intercostal space and suspended in a pericardial cradle. The Lead II electrocardiogram is monitored continuously on an oscilloscope.

Double bipolar silver-silver chloride electrodes, embedded in an acrylic plaque, are sutured to the surface of the right ventricle. One pair of electrodes delivers the basic pacing stimulus while the second pair of electrodes delivers a gated train of impulses. The sinoatrial node is crushed, and the heart rate is maintained by electrically pacing the ventricle at a rate of 2 cps. The ventricular fibrillation threshold is determined by delivering a train of impulses during the ventricular vulnerable period, starting 50 msec after ventricular activation and lasting 250 msec. The train of impulses, 60 Hz, 2 msec duration, is synchronized to the ventricular pacing stimulus and is delivered 50 msec after every sixth basic driven beat. The current delivered is measured directly on an oscilloscope by recording the voltage drop across a 100 ohm resistor in series with the electrodes. The current intensity is increased by increments of 0.5 mA until ventricular fibrillation develops. The ventricular fibrillation threshold is defined as the minimum current in milliamperes (mA) of the test pulse which induce ventricular fibrillation. When fibrillation ensues, the heart is immediately defibrillated using a capacitor DC defibrillator (Physio-Control series 70). Thresholds are determined before and after administration of test compound, 10 mg/kg. Results are compared using Student's t-test for paired comparisons.

The novel compositions of this invention consist of one of the aforementioned active ingredients combined with a pharmaceutically acceptable carrier. These compositions can be administered either orally or parenterally. For oral administration tablets, lozenges, capsules, dragees, pills or powders are suitable, while aqueous solutions, non-aqueous solutions or suspensions are appropriate for parenteral administration. Acceptable pharmaceutical carriers are exemplified by gelatin capsules, sugars such as lactose or sucrose, starches such as corn starch or potato starch, cellulose derivatives such as sodium carboxymethyl cellulose, ethyl cellulose, methyl cellulose or cellulose acetate phthalate, gelatin, talc, calcium phosphate such as dicalcium phosphate or tricalcium phosphate, sodium sulfate, calcium sulfate, polyvinylpyrrolidone, acacia, polyvinyl alcohol, stearic acid, alkaline earth metal stearates such as magnesium stearate, vegetables oils such as peanut oil, cottonseed oil, sesame oil, olive oil, corn oil or theobroma, water, agar, alginic acid, benzyl alcohol, isotonic saline and phosphate buffer solutions as well as other non-toxic compatible substances.

The instant method for reversing arrhythmias in mammals comprises the administration of a novel composition of this invention containing a therapeutically effective amount of the active ingredient. The term "therapeutically effective amount" is defined as the amount of active ingredient that will produce an antiarrhythmic effect. For a particular subject the actual amount of active ingredient to be used will vary with the nature of the subject, the severity of the arrhythmia, the route of administration and the particular active ingredient used. A recommended dosage range for parenteral, e.g. intravenous, administration is 1–10 mg., repeated as needed. For oral administration, a dosage range of 40–500 mg/day is preferred.

The compositions of the present invention can be used also in combination with other known pharmaceutical agents. For example, they can be used together with known anti-anginal agents such as the long-acting nitrites. They can, furthermore, be utilized in combination with other known anti-arrhythmic agents such as quinidine. In addition, they can be used in combination with known hypotensive agents.

The invention will appear more fully from the examples which follow. They are not to be construed as limiting the invention either in spirit or in scope as variations both in materials and in methods will be apparent to those skilled in the art. In the following examples, temperatures are given in degrees Centigrade (°C.) and quantity of materials in parts by weight unless parts by volume is specified.

EXAMPLE 1

34.0 grams (0.20 moles) of 2-phenylphenol and 10.2 grams (0.25 moles) of sodium hydroxide are dissolved in 250 ml of water. The reaction mixture is cooled in ice and 25.0 g (2.27 moles) of epichlorohydrin is added slowly with stirring. Stirring is continued at room temperature for about 42 hr. Then the mixture is extracted with chloroform and the chloroform extracts washed with water until neutral. The chloroform extract is dried over anhydrous potassium carbonate and the solvent evaporated under reduced pressure. There is afforded thereby 2,3-epoxy-1-(2-phenylphenoxy)propane as a blue-green oil.

EXAMPLE 2

Substitution of an equivalent quantity of 3-phenylphenol in the procedure of Example 1 affords 2,3-epoxy-1-(3-phenylphenoxy)propane as an amber oil.

EXAMPLE 3

Substitution of an equivalent quantity of 4-phenylphenol and replacing sodium hydroxide by potassium hydroxide in the procedure of Example 1, affords 2,3-epoxy-1-(4-phenylphenoxy)propane as a white solid melting at about 112°–116° C.

EXAMPLE 4

22.7 g (0.1 mole) of 2,3-epoxy-1-(2-phenylphenoxy)propane is dissolved in 30 ml of methanol. Then 15 ml (0.2 moles) of methylisopropylamine is added to the reaction mixture slowly while stirring. The mixture is refluxed over a steam bath for 48 hr after which time the solvent and excess amine are evaporated under reduced pressure. The residue remaining is dissolved in 200 ml of ether and the solution washed with water. The ether phase is extracted with 5% aqueous hydrochloric acid and the aqueous extracts washed once with ether. The aqueous phase is neutralized with ammonium hydroxide, then extracted with methylene chloride. The methylene chloride extract is dried over anhydrous potassium carbonate and the solvent evaporated under reduced pressure to afford 1-(N-isopropyl-N-methylamino)-3-(2-phenylphenoxy)-propan-2-ol, as a blue-green oil.

EXAMPLE 5

When an equivalent quantity of 2,3-epoxy-1-(3-phenylphenoxy)propane is substituted in the procedure of Example 4, there is obtained, as an amber oil, 1-(N-isopropyl-N-methylamino)-3-(3-phenylphenoxy)propan-2-ol.

EXAMPLE 6

By substituting an equivalent quantity of 2,3-epoxy-1-(4-phenylphenoxy)propane and 30 ml of a 1:1 methanol-chloroform solution in the procedure of Example 4, there is afforded 1-(N-isopropyl-N-methylamino)-3-(4-phenylphenoxy)propan-2-ol.

EXAMPLE 7

To a solution of 10.0 g (0.033 moles) of 1-(N-isopropyl-N-methylamino)-3-(2-phenylphenoxy)propan-2ol and 30 ml of acetone, placed in a pressure container cooled in a Dry Ice-acetone bath is added 30 ml of methyl chloride. The container is sealed and mixture stirred at room temperature for about 8 days, after which time the mixture is again cooled in a Dry Ice-acetone bath. The container is opened slowly to permit reduction of any excess pressure and the solvent and excess methyl chloride is removed by evaporation under reduced pressure. The material remaining is dissolved in 30 ml of absolute ethanol, which then is evaporated under reduced pressure. The latter procedure is repeated and the residue is crystallized from anhydrous acetone to afford [3-(2-phenylphenoxy)-2-hydroxypropyl]isopropyldimethylammonium chloride melting at about 124°–127° C. and represented structurally by the following formula

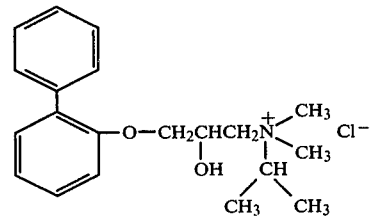

EXAMPLE 8

Substitution of an equivalent quantity of 1-(N-isopropyl-N-methylamino)-3-(3-phenylphenoxy)propan-2-ol in the procedure of Example 7 yields [3-(3-phenylphenoxy)-2-hydroxypropyl]isopropyldimethylammonium chloride, melting at about 254°–256° C. That compound is represented by the following structural formula

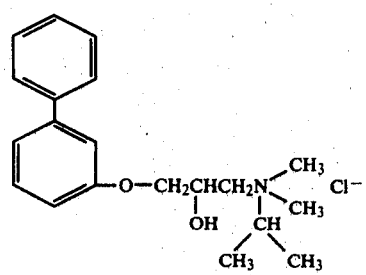

EXAMPLE 2

By substituting an equivalent quantity of 1-(N-isopropyl-N-methylamino)-3-(4-phenylphenoxy)propan-2-ol in the procedure of Example 7, there is obtained [3-(4-phenylphenoxy)-2-hydroxypropyl]isopropyldimethylammonium chloride, melting at about 254°–256.5° C. and represented by the following formula

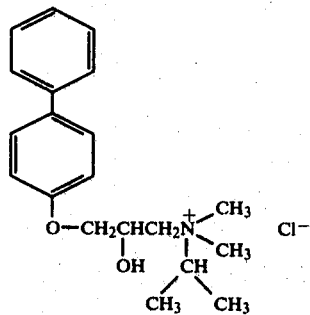

By substituting an equivalent quantity of dimethylamine in place of the methylisopropylamine utilized in Example 4 and subsequently following the procedures of Example 4 and Example 7, there is produced [3-(2-phenylphenoxy(-2-hydroxypropyl]trimethylammonium chloride.

EXAMPLE 11

Substitution of an equivalent quantity of ethylisopropylamine for the methylisopropylamine utilized in Example 4 and subsequently following the procedures outlined in Example 4 and Example 7 affords [3-(2-phenylphenoxy)-2-hydroxypropyl]ethylisopropylmethylammonium chloride.

EXAMPLE 12

Substitution of an equivalent quantity of methyl iodide in the procedure of Example 7 affords [3-(2-phenylphenoxy)-2-hydroxypropyl]isopropyldimethylammonium iodide.

What is claimed is:

1. A pharmaceutical composition which comprises a therapeutically effective anti-arrhythmic amount of a compound of the formula

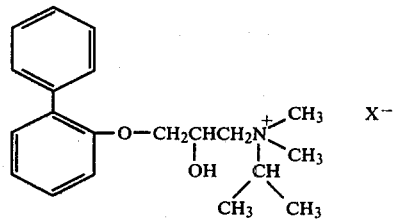

wherein $X^-$ is a chloride, bromide, iodide, fluoride, sulphate, alkylsulphate, or ortho, meta or pyrophosphate anion.

2. A pharmaceutical composition as in claim 1 which comprises a therapeutically effective amount of [3-(2-phenylphenoxy)-2-hydroxypropyl]isopropyldimethylammonium chloride.

* * * * *